United States Patent [19]

Silva et al.

[11] Patent Number: 5,011,966

[45] Date of Patent: Apr. 30, 1991

[54] LOW PHOSGENE METHOD FOR PREPARING AROMATIC BISCHLOROFORMATES

[75] Inventors: James M. Silva, Clifton Park; Thomas J. Fyvie, Schenectady, both of N.Y.

[73] Assignee: General Electric Company, Schenectady, N.Y.

[21] Appl. No.: 222,879

[22] Filed: Jul. 22, 1988

[51] Int. Cl.$^5$ .................. C07C 68/02; C07C 69/96
[52] U.S. Cl. ................... 558/268; 528/372; 558/271; 558/281
[58] Field of Search ................ 558/268, 271, 281

[56] References Cited

U.S. PATENT DOCUMENTS 4,737,573  4/1988  Silva et al. .................. 558/281

*Primary Examiner*—Vivian Garner
*Attorney, Agent, or Firm*—William H. Pittman; James C. Davis, Jr.

[57] ABSTRACT

Aromatic bischloroformates are prepared by the reaction of a dihydroxyaromatic compound such as bisphenol A with phosgene in the presence of water, base and an organic liquid such as methylene chloride. Initially, a mixture of the bisphenol, organic liquid and about 5-15% of the total base is prepared, and phosgene is passed into said mixture. The remainder of the base is added initially at a constant rate, and then only when the measured pH of the aqueous mixture is below a targeted value in the range of about 8-11 and in about 5-10% excess with respect to the phosgene then being introduced. This method minimizes hydrolysis of phosgene and formation of such by-products as monochloroformates and hydroxy-terminated polycarbonate oligomers.

13 Claims, No Drawings

LOW PHOSGENE METHOD FOR PREPARING AROMATIC BISCHLOROFORMATES

This invention relates to the preparation of aromatic bischloroformate compositions, and more particularly to a method for their preparation which is economical with respect to phosgene consumption.

Various patents disclose the preparation of bischloroformate oligomers and their conversion to linear polycarbonates. Reference is made, for example, to U.S. Pat. Nos. 3,646,102, 4,089,888, 4,122,112 and 4,737,573. There are various advantages to preparing linear polycarbonates from bischloroformates rather than directly from phosgene, one of which is the relative purity of the products.

According to the aforementioned U.S. Pat. No. 4,737,573, aromatic bischloroformate compositions are prepared by the reaction of phosgene with a dihydroxyaromatic compound in the presence of aqueous base and a substantially inert, substantially water-insoluble organic liquid. The reaction takes place under backmixing conditions (i.e., in a tank reactor) and at controlled pH, the aqueous base being added at a rate to maintain the aqueous phase of the reaction mixture at a pH in the range of 8-11.

The method disclosed in this patent is of particular value because of the conventional equipment employed and the ease of integration of bischloroformate preparation with its conversion to linear polycarbonates or cyclic polycarbonate oligomers. A disadvantage often encountered, however, is lack of economy in the utilization of phosgene by reason of hydrolysis thereof. Thus, the examples in that patent directed to bischloroformate preparation employ 1.5 moles of phosgene per mole of dihydroxyaromatic compound, corresponding to the stoichiometric ratio for the dimeric carbonate bischloroformate. This is true despite the fact that the average degree of polymerization in most of the examples is greater than 2, and should result in phosgene consumption in lower proportions.

The following equations represent the stoichiometry of bischloroformate preparation and phosgene hydrolysis, using sodium hydroxide as the base:

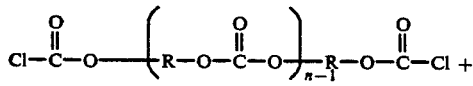

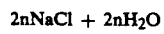

(II) $COCl_2 + 4NaOH \rightarrow Na_2CO_3 + 2NaCl + 2H_2O$    (II)

wherein R is as defined hereinafter and n is the average degree of polymerization of the bischloroformate product. (Other hydrolysis products, such as sodium bicarbonate, are also usually formed.) Thus, the average degree of polymerization is related inversely to the molar ratio of phosgene to dihydroxyaromatic compound and the latter value may be selected to produce bischlofororrmates having the desired average degree of polymerization.

It is also apparent from equation I that the theoretical molar ratio of base to dihydroxyaromatic compound is always 2:1 and that higher ratios promote phosgene hydrolysis. As a practical matter, hydrolysis is also promoted at very low pH levels, since the bischloroformate-forming reaction becomes so slow that it cannot effectively compete for phosgene.

The present invention is based on the discovery that, from the standpoint of phosgene consumption, the pH level is in many respects a secondary factor to the molar ratio of base to dihydroxyaromatic compound. Thus, phosgene hydrolysis and formation of such incidental products as monochloroformates and hydroxy-terminated polycarbonate oligomers are minimized by employing a reaction procedure in which primary attention is given to maintaining said molar ratio near stoichiometric, with only secondary attention being directed to the pH.

Accordingly, the present invention is a method for preparing an aromatic bischloroformate composition which comprises effecting contact at a temperature in the range of about 15°-50° C. between at least one dihydroxyaromatic compound, phosgene, water, an alkali or alkaline earth metal base and a substantially inert, substantially water-insoluble organic liquid, the total molar ratios of phosgene and base to dihydroxyaromatic compound being in the ranges of about 1.1-1.5:1 and about 2.0-2.4:1, respectively, and the total volume ratio of aqueous phase to organic liquid being in the range of about 0.5-1.0:1; said contact being effected by:

preparing a mixture of dihydroxyaromatic compound, organic liquid and about 5-15% of the total base employed;

passing phosgene into said mixture for a period of about 10-30 minutes;

simultaneously introducing the remainder of the base, at a constant rate initially to attain a pH of the aqueous phase of said mixture above a targeted value in the range of about 8-11, and then only when the measured pH falls below the targeted value and at a rate about 5-10% in excess of the amount required to convert the phosgene then being introduced to bischloroformates;

ceasing base addition when phosgene addition is complete, and recovering said bischloroformate composition.

The bischloroformate compositions prepared by the method of this invention comprise mixtures of compounds of varying molecular weight, said compounds having the formula

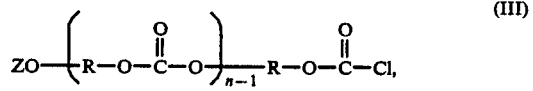

wherein R is a divalent aromatic radical, Z is hydrogen or

and n is at least 1. For many purposes, the proportion of monochloroformate (Z is hydrogen) should be minimized and the invention permits such minimization. It is also generally desirable to maximize the proportion of bischloroformates in which n is from 1 to about 7, at the expense of such by-products as higher bischloroformates, unreacted dihydroxyaromatic compound and hydroxy-terminated polycarbonate oligomers.

These bischloroformate compositions are prepared from dihydroxyaromatic compounds having the formula HO—R—OH. The R values may be aromatic hydrocarbon or substituted aromatic hydrocarbon radicals, with illustrative substituents being alkyl, cycloalkyl, alkenyl (e.g., crosslinkable-graftable moieties such as allyl), halo (especially fluoro, chloro and/or bromo), nitro and alkoxy.

The preferred R values have the formula

$$-A^1-Y-A^2- \qquad (IV)$$

wherein each of $A^1$ and $A^2$ is a monocyclic divalent aromatic radical and Y is a bridging radical in which one or two atoms separate $A^1$ from $A^2$. The free valence bonds in formula II are usually in the meta or para positions of $A^1$ and $A^2$ in relation to Y.

In formula IV, the $A^1$ and $A^2$ values may be unsubstituted phenylene or substituted derivatives thereof wherein the substituents are as defined for R. Unsubstituted phenylene radicals are preferred. Both $A^1$ and $A^2$ are preferably p-phenylene, although both may be o- or m-phenylene or one o- or m-phenylene and the other p-phenylene.

The bridging radical, Y, is one in which one or two atoms, preferably one, separate $A^1$ from $A^2$. It is most often a hydrocarbon radical and particularly a saturated $C_{1-12}$ aliphatic or alicyclic radical such as methylene, cyclohexylmethylene, [2.2.1]bicycloheptylmethylene, ethylene, ethylidene, 2,2-propylidene, 1,1-(2,2-dimethylpropylidene), cyclohexylidene, cyclopentadecylidene, cyclododecylidene or 2,2-adamantylidene, especially an alkylidene radical. Aryl-substituted radicals are included, as are unsaturated radicals and radicals containing atoms other than carbon and hydrogen; e.g., oxy groups. Substituents such as those previously enumerated may be present on the aliphatic, alicyclic and aromatic portions of the Y group.

For the most part, the suitable compounds include biphenols and especially bisphenols. Illustrative bisphenols and other dihydroxyaromatic compounds are listed in the aforementioned U.S. Pat. No. 4,737,573, the disclosure of which is incorporated by reference herein.

The preferred dihydroxyaromatic compounds are those which are substantially insoluble in aqueous systems at temperatures within the range of 20°–40° C. and pH values in the range of about 1–5. Thus, dihydroxyaromatic compounds of relatively low molecular weight and high solubility in water, such as resorcinol and hydroquinone, are generally less preferred. Bisphenol A (in which Y is isopropylidene and $A^1$ and $A^2$ are each p-phenylene) is often especially preferred for reasons of availability and particular suitability for the purposes of the invention.

Also useful are bisphenols containing ester linkages. These may be prepared, for example, by reacting two moles of bisphenol A with one mole of isophthaloyl or terephthaloyl chloride.

Phosgene, water and at least one substantially inert organic liquid are also employed in the method of tis invention. The solubility of the bisphenol in the organic liquid is usually up to about 0.25 M at temperatures in the range of about 20°–40° C., and preferably up to about 0.1 M. Said organic liquid should generally also be substantially insoluble in water. Illustrative liquids are aliphatic hydrocarbons such as hexane and n-heptane; chlorinated aliphatic hydrocarbons such as methylene chloride, chloroform, carbon tetrachloride, dichloroethane, trichloroethane, tetrachloroethane, dichloropropane and 1,2-dichloroethylene; aromatic hydrocarbons such as benzene, toluene and xylene; substituted aromatic hydrocarbons such as chlorobenzene, o-dichlorobenzene, the chlorotoluenes, nitrobenzene and acetophenone; and carbon disulfide. The chlorinated aliphatic hydrocarbons, especially methylene chloride, are preferred.

Also employed is an alkali or alkaline earth metal base. It is most often a hydroxide such as sodium hydroxide, potassium hydroxide or calcium hydroxide. Sodium and potassium hydroxides, and especially sodium hydroxide, are preferred because of their relative availability and low cost.

It is frequently convenient and preferred to provide base and at least a portion of the water in the form of an aqueous base solution. The concentration of said solution is not critical, although concentrations of at least about 10 M are often preferred to maintain the volume ratio of aqueous phase to organic liquid in the desired range. The use of 50% (by weight) aqueous sodium hydroxide is often convenient.

In the first step of the method of this invention, a mixture is prepared which contains all of the bisphenol and organic liquid to be used, but only a portion of the water and base. The portion of base added at this point is about 5–50% and preferably about 6–10%, and the proportion of water is at least sufficient to dissolve said base.

Phosgene is then passed into the mixture over a period of about 10–30 minutes. The remainder of the base, ordinarily dissolved in the remaining water, is simultaneously introduced. The proportions of phosgene and base are adequate to provide total molar ratios in the ranges of about 1.1–1.5:1 and about 2.0–2.4:1, respectively; most often, the phosgene molar ratio is in the range of about 1.15–1.4:1 and that of base is in the range of about 2.2–2.4:1. Also, the amount of water employed is such as to provide a volume ratio of aqueous phase to organic liquid in the range of about 0.5–1.0:1.

A critical aspect of the invention is the mode of addition of base. In the early portions of the phosgene addition period, typically constituting about the first 5–10% thereof, base is added at a constant rate calculated to raise the pH of the aqueous phase of the reaction mixture above a specific value targeted to afford maximum yield of bischloroformates, with minimum hydrolysis of phosgene and minimum formation of the aforementioned incidental products. The targeted value is in the range of about 8–11, preferably about 8–10 and most preferably about 8.1–8.8.

When a pH level above the targeted value, ordinarily in the range of about 8.8–10.0, has been attained, base addition is discontinued. The pH of the reaction mixture is continuously monitored with base addition being resumed when the measured pH is below the targeted value and again interrupted when said value is attained. Base addition in this stage of the process is at a rate about 5–10% in excess of the stoichiometric amount required per equation I for conversion to bischloroformates of the phosgene then (i.e., at the same time as the portion of base) being introduced.

It will be apparent to those skilled in the art that the interruptions of base addition do not mean that the measured pH never rises above the targeted value. It is normal for said pH to continue to rise after base addition has been interrupted, by reason of the time required for its consumption. When consumption is complete, the pH begins to fall and will continue to fall even after base addition is resumed, until adequate dispersion of the newly added base has been achieved. The successive rises and falls in pH will gradually be damped and will eventually level out entirely by reason of the formation of carbonate and/or bicarbonate, which act as buffers.

It is possible and frequently preferred to use conventional automated equipment for monitoring pH and regulating base addition. Thus, pH detection means such as a pH electrode may be immersed in the reaction mixture and connected to a controlling device which controls a pump regulating base addition. Suitable devices of this type are known in the art. It is also contemplated to vary the base addition rate in proportion to the difference between the targeted value and the measured pH.

By employing a total amount of base which is no greater than 1.2 times theoretical (i.e., a molar ratio to bisphenol of 2.4:1), substantial completion of the reaction is achieved without providing base in so great an amount as to facilitate substantial phosgene hydrolysis. Thus, the amount of phosgene required for conversion of bisphenol to bischloroformate is maintained at or below a molar ratio of about 1.5:1.

When phosgene addition is complete, base addition is also discontinued. At this point, the bischloroformate composition is recovered, with recovery steps normally being limited to separation of the aqueous phase from the organic phase containing the bischloroformates. Further isolation steps may be undertaken if desired but are generally not necessary, especially if conversion to linear or cyclic polycarbonates is intended.

The distributions of the molecular species in the bischloroformate compositions prepared by the method of this invention may be determined by reversed phase high pressure liquid chromatography. The composition is first caused to react with an equimolar mixture of phenol and triethylamine to produce the corresponding phenyl carbonates, which are resistant to hydrolysis under chromatography conditions. The phenyl carbonates are dissolved in a mixture of tetrahydrofuran and water and chromatographed using a relatively non-polar packing, whereupon lower molecular weight constituents are eluted first. For each molecular species, three values are determined and used for identification: the retention time (in minutes); the area under the ultra-violet absorption peak at 254 nm., said peak being uniquely associated with compounds of this type; and the ratio of the areas under the absorption peaks at 285 and 254 nm., which is proportional to the level of hydroxy-terminated oligomers.

The standards used for assignment of retention time, 254 nm. absorption and 285/254 nm. ratio are separately prepared linear compounds including bisphenol A mono- and diphenyl carbonate and the diphenyl carbonate of bisphenol A dimer. Higher oligomers are detected by analogy.

The method of this invention is illustrated by an example employing a tank reactor fitted with an agitator, a condenser cooled to $-18°$ C., dip tubes for addition of phosgene and aqueous base and a pH electrode in a recirculation loop. The pH electrode was connected via an electronic controller to a pump which delivered aqueous base at a regulated flow rate when the measured pH fell below the target value. The reactor was charged with 142 grams (620 mmol.) of bisphenol A, 625 ml. of methylene chloride, 275 ml. of deionized water and 6 ml. of 50% aqueous sodium hydroxide solution.

Phosgene was passed into the mixture for 17 minutes, to a total of 806 mmol. (molar ratio to bisphenol 1.3:1, corresponding to an average degree of polymerization of 3.3). As phosgene addition was begun, additional sodium hydroxide solution was also added, at a constant rate for one minute and subsequently only when the pH fell below the targeted value of 8.5, and at a rate 5-10% in excess with respect to the phosgene then being introduced. A total sodium hydroxide volume of 77 ml. (1463.2 mmol.) was employed. The average pH in the period from 10 to 13 minutes after commencement of phosgene addition was 8.3.

A sample was caused to react with a phenol-triethylamine mixture and analyzed as described hereinabove. The results were compared with four controls.

In control A, the procedure was similar to that of Example 2 of U.S. Pat. No. 4,737,573, the molar ratio of phosgene to bisphenol A was 1.5:1 (average degree of polymerization of 2) and base was added to maintain a substantially constant pH of 8.5. Controls B and C employed the method of this invention except that sodium hydroxide flow was not begun with phosgene passage, but only when the pH fell below the targeted value. In control D, no sodium hydroxide was initially introduced and the targeted value was 9 rather than 8.5.

The parameters employed and the results of these experiments are given in the following table. Bischloroformate and monochloroformate are respectively designated "BCF" and "MCF". "PC oligomer" designates hydroxy-terminated species, including principally unreacted bisphenol A and its dimer and trimer carbonates. Values of n are based on formula III.

|  | Invention | Controls | | | |
| --- | --- | --- | --- | --- | --- |
|  |  | A | B | C | D |
| pH, targeted value | 8.5 | 8.5* | 8.5 | 8.5 | 9.0 |
| pH, average, 10-13 min. | 8.3 | 8.5 | 8.45 | 8.5 | 9.0 |
| Sodium hydroxide, ml.: |  |  |  |  |  |
| Initial | 6 | 0 | 6.2 | 7.0 | 0 |
| Total | 77 | 89.8 | 76 | 82 | 83 |
| Molar ratios: |  |  |  |  |  |
| NaOH/bisphenol A | 2.36 | 2.75 | 2.32 | 2.51 | 2.54 |
| Phosgene/bisphenol A | 1.3 | 1.5 | 1.3 | 1.3 | 1.3 |
| Percent COCl$_2$ hydrolyzed** | 6.7 | 12.5 | 6.1 | 9.8 | 10.4 |
| Product distribution, mole %: |  |  |  |  |  |
| PC oligomer | 0.4 | 15.6 | 3.6 | 20.8 | 18.9 |
| MCF: |  |  |  |  |  |
| n = 0 | 2.4 | 16.9 | 7.1 | 22.0 | 16.4 |
| n = 1 | 5.6 | 17.9 | 8.9 | 15.7 | 16.1 |
| BCF: |  |  |  |  |  |
| n = 0 | 18.0 | 14.4 | 13.7 | 7.9 | 6.8 |
| n = 1 | 28.0 | 22.4 | 25.6 | 19.9 | 24.3 |
| n = 2 | 21.9 | 8.2 | 14.7 | 11.5 | 15.5 |
| n = 3 | 11.6 | 2.0 | 10.3 | 2.2 | 2.0 |
| n = 4 | 7.6 | 1.8 | 6.2 | 0 | 0 |
| n = 5 | 4.5 | 0.8 | 3.1 | 0 | 0 |
| n = 6 | 0 | 0 | 0 | 0 | 0 |
| n = 7 and higher | 0 | 0 | 6.8 | 0 | 0 |

*Average value.
**Calculated from excess NaOH.

It will be seen that the calculated phosgene hydrolysis level was lower for the method of this invention than for any control except Control B, and the proportions of PC oligomer and monochloroformates were lower than for any control. In particular, comparison with Control A shows the benefits of the invention as compared to operating at a constant pH identical to the targeted value.

What is claimed is:

1. A method for preparing an aromatic bischloroformate composition which comprises effecting contact at a temperature in the range of about 15°–50° C. between at least one dihydroxyaromatic compound, phosgene, water, an alkali or alkaline earth metal base and a substantially inert, substantially water-insoluble organic liquid, the total molar ratios of phosgene and base to dihydroxyaromatic compound being in the ranges of about 1.1–1.5:1 and about 2.0–2.4:1, respectively, and the total volume ratio of aqueous phase to organic liquid being in the range of about 0.5–1.0:1; said contact being effected by:

preparing a mixture of dihydroxyaromatic compound, organic liquid and about 5–15% of the total base employed;

passing phosgene into said mixture for a period of about 10–30 minutes;

simultaneously introducing the remainder of the base, at a constant rate initially to attain a pH of the aqueous phase of said mixture above a value in the range of 8–11;

discontinuing base addition while continuing phosgene addition;

resuming base addition when the measured pH falls below said pH value, said resumed base addition being at a rate about 5–10% in excess of the amount required to convert the phosgene then being introduced to bischloroformates;

ceasing base addition when phosgene addition is completed, and recovering said bischloroformate composition.

2. A method according to claim 1 wherein the organic liquid is methylene chloride.

3. A method according to claim 2 wherein the base and at least a portion of the water is provided in the form of an aqueous base solution.

4. A method according to claim 3 wherein the base is sodium hydroxide.

5. A method according to claim 4 wherein the dihydroxyaromatic compound has the formula $HO-A^1-Y-A^2-OH$, wherein each of $A^1$ and $A^2$ is a monocyclic divalent aromatic radical and Y is a bridging radical in which one or two atoms separate $A^1$ from $A^2$.

6. A method according to claim 5 wherein the total molar ratios of phosgene and base to dihydroxyaromatic compound are in the ranges of about 1.15–1.4:1 and about 2.2–2.4:1, respectively.

7. A method according to claim 6 wherein said pH value is in the range of about 8–10.

8. A method according to claim 7 wherein the dihydroxyaromatic compound is bisphenol A.

9. A method according to claim 7 wherein said pH value is in the range of about 8.1–8.8.

10. A method according to claim 9 wherein the concentration of the base solution is at least about 10 M.

11. A method according to claim 10 wherein about 6–10% of total base is initially present.

12. A method according to claim 11 wherein base is added at a constant rate during about the first 5–10% of the phosgene addition period.

13. A method according to claim 12 wherein the dihydroxyaromatic compound is bisphenol A.

* * * * *